United States Patent
Kennedy

(10) Patent No.: US 9,233,030 B1
(45) Date of Patent: Jan. 12, 2016

(54) MOISTURE ALERT PAD (M.A.P.), MOISTURE ALERT PAD PILLOWCASE (M.A.P.P.), AND MOISTURE ALERT PAD VEST (M.A.P.V.)

(71) Applicant: Kyra Massey Kennedy, Douglasville, GA (US)

(72) Inventor: Kyra Massey Kennedy, Douglasville, GA (US)

(73) Assignee: Kyra Massey Kennedy, Douglasville, GA (US)

( * ) Notice: Subject to any disclaimer, the term of this patent is extended or adjusted under 35 U.S.C. 154(b) by 0 days.

(21) Appl. No.: 14/170,934

(22) Filed: Feb. 3, 2014

Related U.S. Application Data

(60) Provisional application No. 61/850,096, filed on Feb. 8, 2013.

(51) Int. Cl.
*G08B 21/20* (2006.01)
*A61F 13/42* (2006.01)

(52) U.S. Cl.
CPC ..................................... *A61F 13/42* (2013.01)

(58) Field of Classification Search
CPC .... A61F 13/42; G08B 21/0211; G08B 21/12; G08B 21/20; G08B 21/0469
USPC ............... 340/604, 539.14; 600/382; 128/886
See application file for complete search history.

(56) References Cited

U.S. PATENT DOCUMENTS

| | | | | |
|---|---|---|---|---|
| 3,810,140 | A * | 5/1974 | Finley .................. | A61F 5/48 128/886 |
| 3,864,676 | A * | 2/1975 | Macias et al. ............. | 600/382 |
| 4,020,478 | A * | 4/1977 | Hatfield ................ | G08B 21/20 340/604 |
| 4,163,449 | A * | 8/1979 | Regal .................. | A61F 5/48 128/886 |
| 5,192,932 | A * | 3/1993 | Schwab, Jr. ........... | G08B 21/20 324/693 |
| 6,639,517 | B1 * | 10/2003 | Chapman ............... | G01M 3/16 137/312 |
| 8,144,021 | B2 * | 3/2012 | Page .......................... | 340/604 |
| 8,508,373 | B2 * | 8/2013 | Rice ........................... | 340/603 |
| 2004/0106202 | A1 * | 6/2004 | Zainiev et al. ............. | 436/39 |
| 2006/0261963 | A1 * | 11/2006 | Giles et al. ................ | 340/604 |
| 2009/0284382 | A1 * | 11/2009 | Hill ............................. | 340/604 |
| 2009/0322543 | A1 * | 12/2009 | Crnkovich et al. ........ | 340/604 |
| 2012/0256750 | A1 * | 10/2012 | Novak ..................... | 340/573.5 |

\* cited by examiner

*Primary Examiner* — Albert Wong
(74) *Attorney, Agent, or Firm* — Paul K. Judd; Lilenfeld PC

(57) ABSTRACT

A moisture alert device that has a number of moisture detecting sensor divots around the outside of the device where the sensor divots are connected to insulated circuits within the device that transmits a moisture detections signal to a base, the base sending the signal to a control device, which in turn sends the moisture detection signal to a user by visual, auditory or tactile means. In some cases, the moisture detection signal transmitted to a wireless receiving device. The device can be a wearable garment such as a vest, or in other situations, the device can be a bed component such as a pillow case.

15 Claims, 5 Drawing Sheets

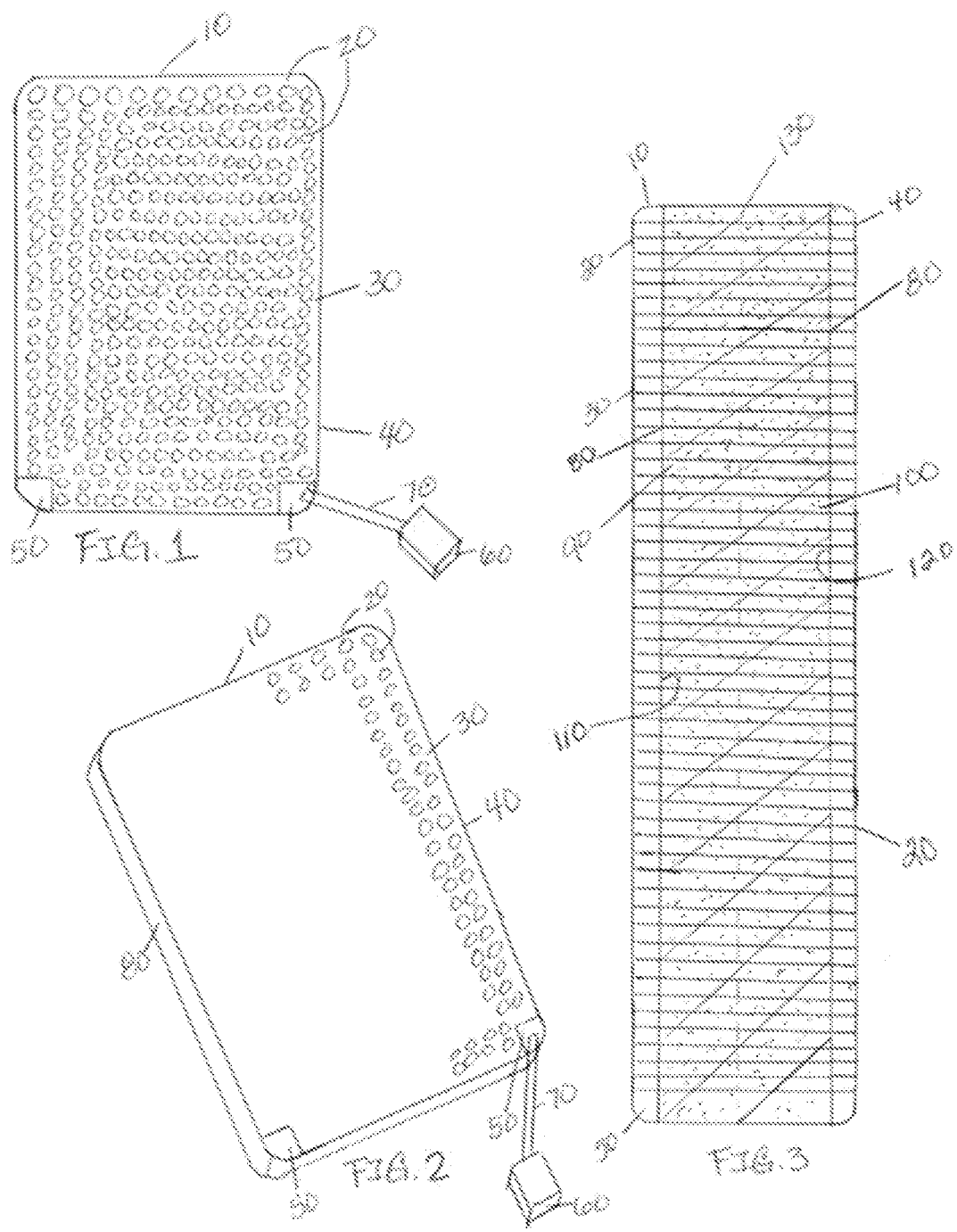

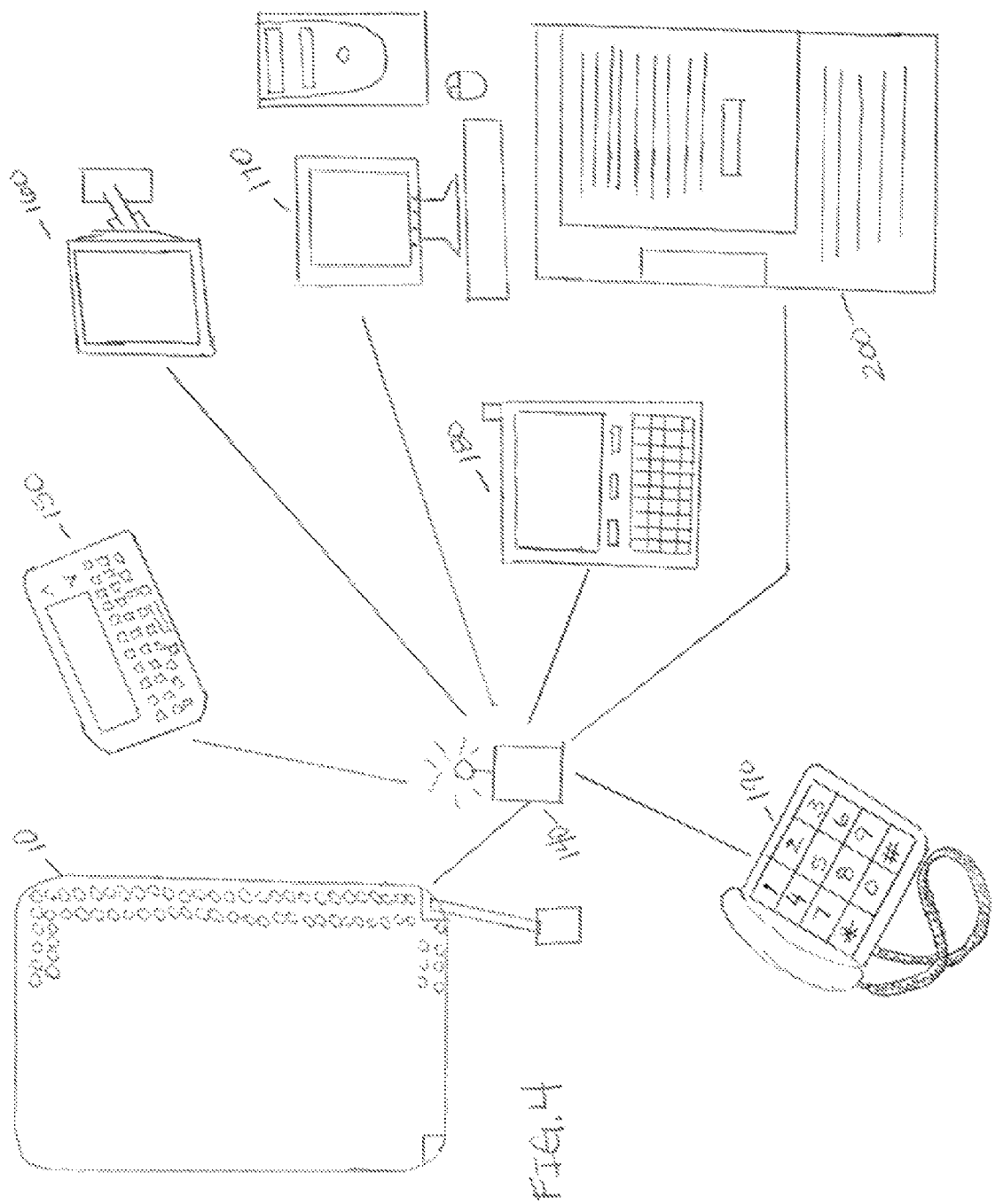

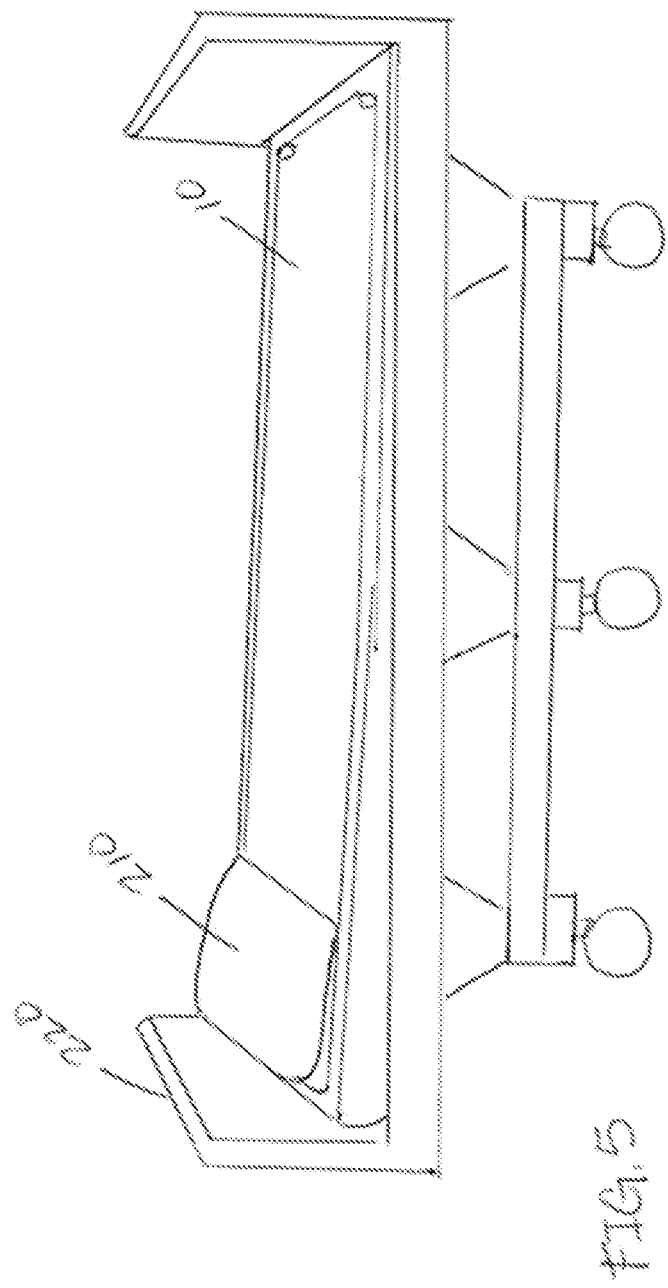

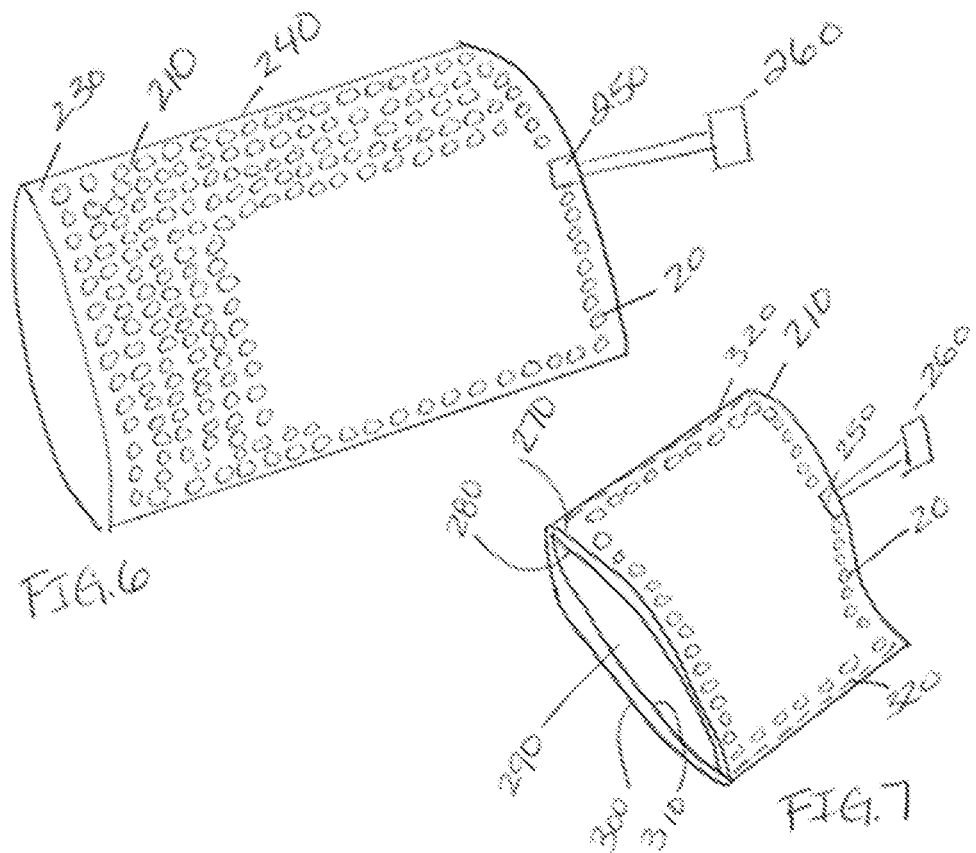
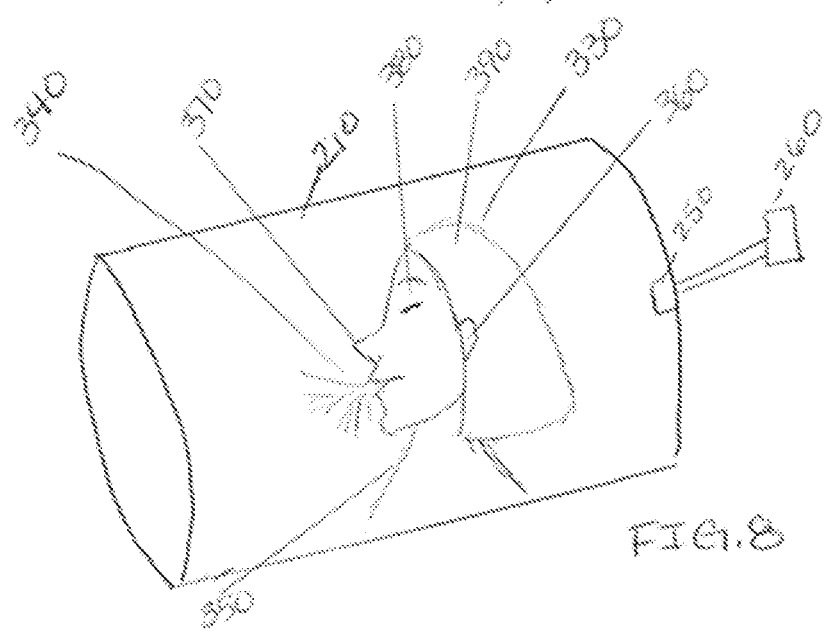

MOISTURE ALERT PAD (M.A.P.), MOISTURE ALERT PAD PILLOWCASE (M.A.P.P.), AND MOISTURE ALERT PAD VEST (M.A.P.V.)

CROSS-REFERENCE TO RELATED APPLICATIONS

This application claims the benefit of U.S. provisional application 61/850,096 filed Feb. 2, 2013 and is herein incorporated by reference in its entirety.

FEDERALLY SPONSORED RESEARCH

None.

SEQUENCE LISTING OR PROGRAM

None.

BACKGROUND

PREVIOUSLY the inventors created an apparatus for a child who bed wets while sleeping only. The main function of this apparatus is for urine detection only on both sides of the pad. As well as creating an alarm to notify wetness detection.

Previously invented pads focused only on urine of children and/or adults who wet their beds on a constant basis. They included electrical circuits with an alarm which activate the alarm to detect small amount of urine. The alarm will then de-activate within a few minutes if it's below a certain amount of urine. The patent is specific for children who urinate in bed. The apparatus has to be at a certain amount of urine to prompt the alarm to go off.

Originally the patent is designed to treat children for bed wetting issues. The pad comes with a loud alarm and bright light for notification. The first alarm is loud which includes a spotlight. The second alarm will awaken the caregiver or nurse monitoring the specific pad. There is a 20 minute delay to notify caregiver that the alarm for bed wetting has gone off. This particular design will provide a count of the number of bed wetting occurrences that night.

The main programming system of one pad is an electronic 12 stepper relay. Programming this invention can be set off by a large alarm or 20 minute delay alarm. The alarm has options for reinforcement and non-reinforcement trials.

However, the lighting on the invention has a service light which can be turn off until reactivated. The purpose of the light on the pad is to remind the caregiver to reactivate the alarm. The light will let you know that urine on the pad has been detected even when the alarm is deactivated.

The main source for the inventions is urine detection and there is no other detection for moisture whether water and/or any moisture substances. The pad only provides detection for a small amount of space. The invention notification is limited to alarms for the child and for the caregiver.

The apparatus in U.S. Pat. No. 3,810,140 to Finley, 1974 May 7, had limited options regarding moisture detection. Originally the apparatus treat patients who had problems bedwetting only. In the summary of the invention of U.S. Pat. No. 3,810,140, primary objective is to provide an apparatus which will treat children for bedwetting. The problem had been partially solved by the implementation of this pad, but this still has not solved the detection of other types of moisture issues. This pad does not allow people of all ages, animals, equipment and objects that release moisture or any liquid substance, which may need assistance in detecting other moisture substances. As well as notify of the detection with wireless technology capabilities.

The U.S. Pat. No. 3,810,140 failed to solve the problem for other moisture detection and a solution is very well needed. This inventor did not think about, animals, infants, adults, equipment, elderly or anyone who is bedridden and/or unable to walk or talk that may need detection for mucus, blood, vomit or any moisture that may or may not be hazardous and/or harmful to the person or animals on the pad. Also the inventor did not think whether a piece of equipment or object that may leak which can cause huge liquid damage.

Performance of the apparatus in U.S. Pat. No. 3,810,140 operates by battery. An apparatus with more detection options need to operate with battery and electric socket options. This U.S. Pat. No. 3,810,140 had a limited number of options with a transistor located in the bedroom of the parent. The inventor didn't consider a solution for other persons who may need to be notified of other types of moisture than urine to be detection using the pad. A solution is needed for these types of situations.

The U.S. Pat. No. 3,810,140 only use three types of notification for urine bedwetting, which are loud bell; a "blue" spotlight and an alarm to awaken patient's caregiver. Finally, Finley did not consider all types of reasons why other people may need notification for other types of moisture other than urine. As well as provide notification for people who are not just caretakers, patients or children.

U.S. Pat. No. 4,163,449 to Regal, 1979 Aug. 7, disclosed another type of pad only could be used for a child who bed wets while asleep with urine detection only. Regal did not consider moisture detection for other types of moisture as well as person of all ages, animals, equipment and other objects who are not specifically asleep and need close monitoring. This is not effective in helping to detect other moisture incidents that may occur outside of bedwetting incidents.

The pad in U.S. Pat. No. 4,163,449 disclosed an aversive stimulus notification to a child depending on a certain amount of urine exposed. This pad does not effectively detect if the moisture is not urine and some other type of moisture.

Regal pad does not allow persons of all ages, animals, equipment and other objects and moistures of any type to be properly detected. The pad only could be used for detection by placing the pad beneath a bed sheet.

SUMMARY

In accordance with the present invention, a moisture pad, pillowcase and vest comprise of flat sensor divots all over the pads can detect any type of moisture when in direct contact. Accordingly the reader will see that, according to this invention, I have provided multiple highly reliable and lightweight economical devices for moisture detection. That can be used by people of all ages; any object or equipment that releases moisture; and animals as well. I have explained of the Moisture Alert Pad (M.A.P.), Moisture Alert Pad Pillowcase (M.A.P.P.) and Moisture Alert Pad Vest (M.A.P.V.) can detect any type of moisture whether it is urine, blood, sweat, water, vomit, toxic substance etc. from a person, animal, equipment and/or object. The moisture has to be directly in contact of the moisture alert pad, moisture alert pad pillowcase and/or moisture alert pad vest. Once moisture has been detected, notification will be sent through the electronic communication devices and/or to the wireless transmitting options. The Moisture Alert Pad Vest (M.A.P.V.) has a design for the Armed Forces and/or any person monitoring persons and/or soldiers closely to detected high perspiration and other duress signs via specially designed circuits and other technology on the inside layers of the vest. Furthermore, the moisture alert pad, moisture alert pad pillowcase and moisture alert pad vest have additional advantages in that:

They permit the production of new technology to monitor moisture being released on the pad, pillowcase and/or vest.

They allow a person, animal, equipment and/or object once they release moisture to notify the monitor with wireless technology and monitoring options.

They provide monitoring with the pillowcase for duress patient that need intense monitoring from the neck and above, along with full body monitoring.

They provide immediate notification if a person is bedridden and has bed-wetting issues that may need changing of material due to soiled garments from urine, blood, vomit, sweat, etc.

They allow the production of other shapes and sizes to meet most detecting needs.

They provide moisture detection for hot water heaters, pipes and any equipment that may have a leakage problem or may require preventive leakage monitoring.

They provide notification for high perspiration and other duress signs for soldiers in intense climates for close monitoring situations.

They permit the use of monitoring on any flat surface, mattress, and area with an incline, movable and portable surfaces.

They notify that a leakage has occurred via email, text messages, voice callings and other wireless technology viewable and communication devices for notification.

They provide immediate notification that can mean the difference in seconds of the monitor saving a life where needed.

While the above description contains many specifications, this should not be construed as limitations on the scope of the invention, but as exemplifications of the presently preferred embodiments thereof. Many other ramifications and variation are possible within the teachings of the invention. For example, the pad can detect any type of moisture; the pillowcase can detect any type of moisture; and the vest can detect any type of moisture. The monitor can be notified by vibration, sounds, alerts, wireless options, data transmitting, wireless devices and other devices; the pad, pillowcase and vest can used by infants, children, teens, adults, elderly, animals, objects, etc. The pad can be used in positions such as but not limited to on, under, around equipment and objects.

Thus the scope of the invention should be determined by the appended claims and their legal equivalents, rather than by the examples given.

DRAWINGS

Figures

FIG. 1 shows various aspects of the moisture alert pad with electronic controlling device.

FIG. 2 shows a perspective view of the moisture alert pad with electronic controlling device.

FIG. 3 shows an enlarged internal view and side view of the moisture alert pad.

FIG. 4 shows the moisture alert pad in its various types of technology that can receive and transmit data with the pad.

FIG. 5 shows one of the various and most preferred uses for the moisture alert pad in combination with the moisture alert pad pillowcase.

FIG. 6 shows various aspects of the moisture alert pad pillowcase with electronic controlling device.

FIG. 7 shows a perspective view of the moisture alert pad pillowcase with electronic controlling device.

FIG. 8 shows a perspective view and main usage of the moisture alert pad pillowcase.

DETAILED DESCRIPTION

Figure 9:
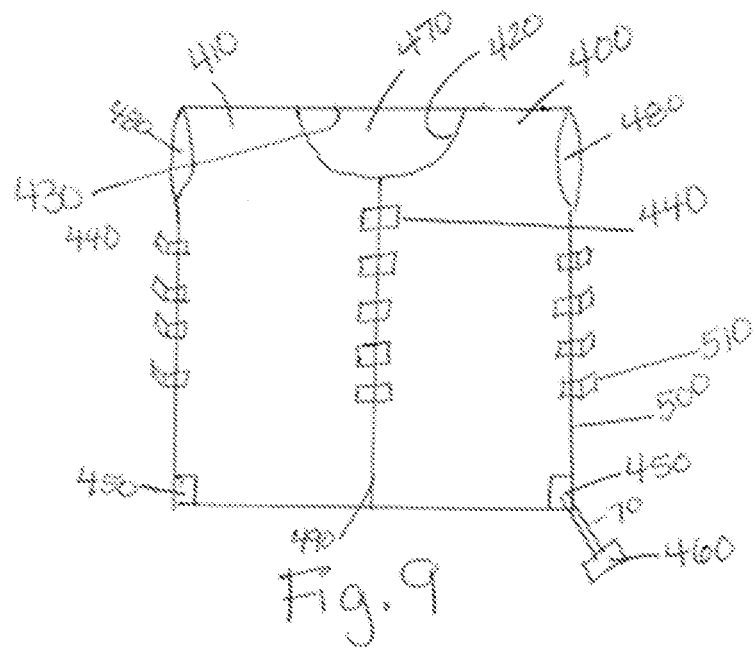
FIG. 9 shows various aspects of the moisture alert pad vest with electronic controlling device.
Figure 10:
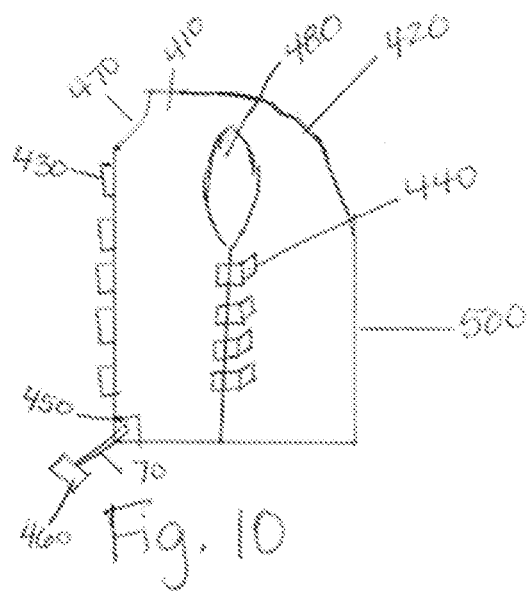
FIG. 10 shows a side view of the moisture alert pad vest.

The Moisture Alert Pad (M.A.P.) which is the subject of this disclosure is generally shown in the drawings by the reference numeral (10). As shown in (FIG. 1), the drawing of pad (10) is designed to detect moisture from a person, animal, person bedridden, equipment and/or object releasing moisture needing monitoring. Any type of moisture can be detected, such as urine, blood, vomit, oil, water, oil etc.

The pad (10) works in conjunction with the electronic controlling device (60). The pad (10) can be placed above or below the sheets for accurate detection. Or the pad (10) can be placed under hot water heater and/or around pipes for detection as well. The side-1 insulated surface (90) and side-2 insulated surface (100) has many identical sensor divots (20) registered throughout the pad (10) located on each side of pad (10). The moisture reaches the many sensor divots (20) located thru out the pad (10). When moisture reaches the sensor divots (20) on its surface, the insulated circuits (80) send signals that moisture has been detected. The signal contacts the electronic base (50) to provide a moisture alert. Through cord (70) signals to electronic controlling device (60) to provide a visible, sound and/or transmit data to have an alarm goes off to acknowledge moisture has been detected. This pad (10) can be used by a person, animal, equipment or object needing moisture detection, and will stay in place without needing attachments to hold it in place. When in direct contact of any moisture from the user within the perimeter of the pad (10), it then sets off notifications. The device shown at (60) can be operated by batteries or electrical outlet. The Electronic Controlling Device (60) has adjustable settings which include but not limited to vibration, light, wireless notifications and other sound notifications to alert the user in direct contact on the pad (10). As well as notify the monitor that leakage has immediately occurred. The main functions of Electronic Controlling Device (60), is to transmit the alerts and data to those who are using the pad (10) and are monitoring the user. There is an automatic kill switch as well. The pad (10) is made up of a side-1 layer (30) and side-2 layer (40). Both sides can provide moisture detection. The material involved has a smooth upper and lower surface. The pad (10) material is made from a soft flexible type surface.

Once the moisture is detected thru the sensor divots (20) on the side-1 layer (30) or side-2 layer (40), the electronic detecting insulated circuits (80) located thru layers (30) and (40) signals to electronic base (50). The electronic base (50) is connected to a detachable cord (70). Then the Electronic Controlling Device (60) alerts are then setoff by the sound, vibration, light and/or other wireless and non-wireless notification it is set under. The insulated surfaces (90) and (100) are protected by the side-1 Inside Conductive Layer (110) and side-2 Inside Conductive layer (120), which are located on both sides of the phantom line (130).

In [FIG. 2] shows the perspective side view of pad (10). The Electronic Controlling Device (60) has vibration, light, earphones, wireless earphones, QR code options on the back of the electronic controlling device (60).

The pad (10), insulated surfaces (90) and (100) are of a compressible and flexible material. The material should be nonabsorbent of the moisture to prevent from damaging and/or altering proper moisture detection and alerts. The material for the pad (10) provides a neutral insulating surface (90) and (100) which is electronically nonconductive.

Other sound notification options to alert person lying on the pad (10) and the monitor that moisture has been detected are available. Once detected, the pad (10) immediately alerts who released the moisture, and person observing via a variety of monitoring option [FIG. 4]. After so many alerts, there is an automatic kill switch on electronic controlling devices (60), (260) and (460). The material of the pad (10) is a type of smooth fabricated material that is non-absorbent. The monitoring alert options are not limited to the options in [FIG. 4]. Also Moisture Alert Pad Pillowcase (210) and Moisture Alert Pad Vest (M.A.P.V.) (400) have the same technology options in [FIG. 4]. All devices are not limited to only the technology shown in [FIG. 4] or in this claim.

The side-1 Insulating surface (90) is between Insulated Circuit (110) and (130) which is the Phantom Surface (130) between both layers. The layer (120) is considered another layer which operates as another moisture detection option. Side-1 layer (30) and side-2 layer (40) provides the same detection regardless of which side the pad is on. The inner layer (30) and (40) are bonded together permanently. The layers (110) and (120) stretch continuously across side-1 layer (30) and side-2 layer (40) of the pad (10). Many identical sensor divots (20) are located throughout and facing outward of the pad (10). Also pad (10) is designed to allow proper moisture and/or liquid substance detection. The layers (30) and (40) are located in direct contact of the moisture. The sensors divots (20) are of circular shape with open cup-like pockets formed throughout the pad (10). The thickness and radius of (20) are suitable for proper and accurate moisture detection. The phantom line (130) describes the high percentage depth of the pad (10). To insure the detection of moisture is identified immediately, the sensors divots (20) are arranged in continuous patterns throughout layers (30) and (40) on pad (10), pillowcase (210) and vest (400).

As illustrated in [FIG. 1] and [FIG. 2], the electronic base (50) is permanently attached to the layers (30) and (40) on the pad (10), pillowcase (210) and vest (400). Once the base (50) has been notified of moisture detection, it signals thru cord (70) which allows the Electronic Controlling Device (60) to respond by sending out electrical signals, wireless signals, alerts, sounds, vibrations etc. to notify person or object that it has detected the releasing of moisture on the pad (10). The wireless signal from the pad (10), pillowcase (210) and vest (400) can send text messages, emails, voice calls and other notification to SMART phones, pads, pagers and other electronic and cordless devices using it's Wi-Fi and wireless technology capabilities. Once the first drop of moisture (which could be urine, blood, water, oil etc.) has been detected thru the sensor (20) and reaches the insulated circuits (80) which sets off the multiple technology options programmed in the electronic controlling device (60). The electronic controlling device (60) is capable of programming to specifically identify that particular Moisture Alert Pad (10), Moisture Alert Pad Pillowcase (210) and Moisture Alert Pad Vest (M.A.P.V.) (400). This action will alert the person, animal, equipment or object who released moisture and signal out other monitoring option in [FIG. 4]. There is a QR code option located on the backside of each Electronic Controlling Devices (60), (260) and (460). QR code option will allow the monitor, caregiver or concerning party use a wireless device, cell phone etc with a QR code reader app or software to locate data on that particular Moisture Alert Pad (10), Moisture Alert Pad Pillowcase (210) and Moisture Alert Pad Vest (M.A.P.V.) (400).

The pad (10) doesn't absorb any moisture that is presented on it. It only detects that moisture or a liquid substance has been released. After proper cleaning, pad (10) restores to its original dry condition by using an absorbent cloth, tissue, paper towel or any absorbent material that is used for drying and/or cleaning. The pad (10) can be placed back to use or flip on the other side for new detection process.

Illustrated in [FIG. 4] is a general description of what happens when pad (10) and Electronic Controlling Device (60) receives alert that moisture has been detected. After notification, the electronic controlling device (60) applies the multiple options of technology and notifications options. The electronic controlling device (60) signals to Receiver/Transmitter Device (140), which could be Wi-Fi, wireless routers and/or other type of data transmitting devices for it to perform multiple technological features, such as texting, emailing and calling features. The Receiver/Transmitter Device has the capability to send text messaging to any wireless electronic devices such as a: wireless pager (150) that moisture has been detected for that particular Moisture Alert Pad (10), Moisture Alert Pad Pillowcase (210) and Moisture Alert Pad Vest (M.A.P.V.) (400). The Receiver/Transmitter Device (140) has capability to be monitored via a wall monitor (160) to alert the monitor that the particular Moisture Alert Pad (10), Moisture Alert Pad Pillowcase (210) and Moisture Alert Pad Vest (M.A.P.V.) (400) that moisture has been detected. The Receiver/Transmitter Device (140) has capability to alert monitor via desktop computer (170), instant messaging, email, and other computerized and wireless options. The Receiver/Transmitter Device (140) have capability to notify the monitor that moisture has been detected on Moisture Alert Pad (10), Moisture Alert Pad Pillowcase (210) and Moisture Alert Pad Vest (M.A.P.V.) (400), via wireless cell phone (180) via texting, instant messaging, email, wireless applications, calling features with computerized voice messaging alerts, etc. The Receiver/Transmitter Device (140) has capability to call on landline phone (190) and notify monitor using a computerized voice messaging system that moisture has been detected on Moisture Alert Pad (10), Moisture Alert Pad Pillowcase (210) and Moisture Alert Pad Vest (M.A.P.V.) (400). The Receiver/Transmitter Device (140) has the capability via Wi-Fi and wireless technology to send, store, monitor and manage multiple Moisture Alert Pad (10), Moisture Alert Pad Pillowcase (210) and Moisture Alert Pad Vest (M.A.P.V.) (400) by using a server (200). Server (200) can produce, send and save the proper programming data to monitor all Moisture Alert Pad (10), Moisture Alert Pad Pillowcase (210) and Moisture Alert Pad Vest (M.A.P.V.) (400). Other capable options for this Moisture Alert Pad (10), Moisture Alert Pad Pillowcase (210) and Moisture Alert Pad Vest (M.A.P.V.) (400) are but not limited to include printing out data, store, compile and send data to wireless options (150), (160), (170), (180) and (190) by using M.A.P., M.A.P.P. and M.A.P.V. down loadable software. This would be helpful if data was requested on how many times a patient, client, animal and/or equipment released moisture (such as blood, water, urine, etc.) while confined to their bed (220) or place of monitored detection. With this new technology for these Moisture Alert Pad (10), Moisture Alert Pad Pillowcase (210) and Moisture Alert Pad Vest (M.A.P.V.) (400) pads' design, such request may also come from clients, person's living at a resident, patients, pet owners, doctor, patient's responsible party who would like a report of how many alerts were sent via the monitoring server (200) or the other technology.

Along with the QR code options on the back of every M.A.P. Electronic Controlling Device (60), M.A.P.P. Electronic Controlling Device (260) and M.A.P.V. Electronic Controlling Device (460) to add quicker access to data as well. Using the QR code reader will take you directly to the stored data website page which can be accessed via a smart phone, tablet, other wireless devices etc.

In [FIG. 5], the Moisture Alert Pad (10) can be made in pillowcase Moisture Alert Pad Pillowcase (210) sizes thus shown, Moisture Alert Pad Pillowcase (210). With the option of Moisture Alert Pad Pillowcase (M.A.P.P.) (210) has the same capability to process moisture alerts for the neck and above. Side-1 View of M.A.P.P. (230) has the same capability as Side-1 Layer (30). Side-2 View of M.A.P.P. (240) has the same capability as Side-2 Layer (40). Electronic Base of M.A.P.P. (250) has the same capability as Electronic Base of M.A.P. (50) and Electronic Base of M.A.P.V (450). Electronic Controlling Device of M.A.P.P. (260) and Electronic Controlling Device of M.A.P.V. (460) have the same capability as Electronic Controlling Device (60).

In [FIG. 7], Side-1 Layer of M.A.P.P. (270) has the same detection capability as Side-2 Layer of M.A.P.P. (300). Side-1 inside Layer of M.A.P.P. (280) and Side-2 inside Layer of M.A.P.P. (310) has the same capability as Side-1 Insulated Layer (90) and Side-2 Insulated Layer (100). Opening for Pillow (290) is the opening where the pillow is placed inside M.A.P.P. (210). The stitching (320) is the manner of how M.A.P.P. (210) is permanently attached together to produce options of a pillowcase.

Illustrated in [FIG. 8] is an appearance of a person (330). A person or user will have complete moisture detection from the neck and above. Using M.A.P.P. (210), a person (330) can be monitored for moisture such as vomit, blood, stomach acid, etc., basically any moisture from the mouth (340). With M.A.P.P. (210) having sensors divots (20) continuously throughout the pillowcase, if a person (330) that was releasing mucus, blood, or any moisture from: mouth (340); above the neck (350); from the ears (360); nose (370); the eyes (380), any moisture above the neck can be detected. M.A.P.P. (210) would detect any moisture and/or bodily fluids as well. If a person or object need monitoring for blood, fluid, and any moisture from the head (390) and surrounding areas, M.A.P.P. (210) will function as if it's Moisture Alert Pad (10) and process alerts thru the multiple technological options in [FIG. 4].

Illustrated in [FIG. 9] is a view of Moisture Alert Pad Vest (M.A.P.V.) (400) that can be placed on a person who is bedridden or need close monitor of the upper body. The top layer of M.A.P.V. (410) facing upward is the most effective way of the vest to be worn. The inside detection layer (420) and inside back detection layer (430) uses the same sensor divots (20) and processes as Moisture Alert Pad (10). The front latches (440) and side latches (510) are adjustable to fit patient snug for better support. The electronic base of (M.A.P.V.) (450) works exactly the same as (50) and (250). The electronic controlling device of (M.A.P.V.) (460) works exactly the same as (60) and (260). (470) is the opening for the neck. As well as (480) is the opening for the arms. The opening of the vest (490) is how the patient or person needing close monitoring in stressful climates would place the vest on his or her upper body. Both (410) which is the outside layer of (M.A.P.V.) and (500) Bottom/Back Layer of (M.A.P.V.) are non-conductive and does not detect moisture. Per design request, both (410) which is the outside layer of (M.A.P.V.) and (500) Bottom/Back Layer of (M.A.P.V.) can be designed to detect moisture as well.

The technology and options of (M.A.P.) (10), (M.A.P.P.) (210) and (M.A.P.V.) (400) are no means limited to various changes that might be made in the device and device wireless options without modifying the basic concept embodied in the structure. For this reason, only the following claims are intended to define the scope of the invention disclosed herein.

DRAWINGS

Reference Numerals

10 Moisture Alert Pad (M.A.P.)
20 Sensor Divots
30 Side-1 Layer
40 Side-2 Layer
50 Electric Base of (M.A.P.)
60 Electronic Controlling Device (M.A.P.)
70 Cord
80 Insulated Circuits
90 Side-1 Insulated Surface
100 Side-2 Insulated Surface
110 Side-1 Inside Conductive Layer
120 Side-2 Inside Conductive Layer
130 Inside Phantom Surface Line
140 Transmitting/Receiving Device
150 Paging device
160 Wall Monitoring Device
170 Desktop Computer or Desk Monitoring Device
180 Wireless Cell Phone Device
190 Landline Phone Device
200 Server Device
210 Moisture Alert Pad Pillowcase (M.A.P.P.)
220 Sample Hospital Bed
230 Side-1 View of (M.A.P.P.)
240 Side-2 View of (M.A.P.P.)
250 Electric Base of (M.A.P.P.)
260 Electronic Controlling Device (M.A.P.P.)
270 Side-1 Layer of (M.A.P.P.)
280 Side-1 Inside Layer of (M.A.P.P.)
290 Opening for Pillow
300 Side-2 Layer of (M.A.P.P.)
310 Side-2 Inside Layer of (M.A.P.P.)
320 Stitching/Gathering
330 Person
340 Perspective Moisture Type from mouth
350 Perspective Moisture Type from neck
360 Perspective Moisture Type from ears
370 Perspective Moisture Type from nose
380 Perspective Moisture Type from eyes
390 Perspective Moisture Type from head
400 Moisture Alert Pad Vest (M.A.P.V.)
410 Top Layer of (M.A.P.V.)
420 Inside Detection Layer of (M.A.P.V.)
430 Inside Back Detection Layer
440 Front Latches with Adjustable belts
450 Electric Base of (M.A.P.V.)
460 Electronic Controlling Device for (M.A.P.V.)
470 Opening for neck
480 Opening for arms
490 Opening of vest
500 Bottom/Back Layer of (M.A.P.V.)
510 Side Latches with Adjustable belts Operation From the description above, a number of advantages of the Moisture Alert Pad (M.A.P.), Moisture Alert Pad Pillowcase (M.A.P.P.), and Moisture Alert Pad Vest (M.A.P.V.) become evident:

(1) The Moisture Alert Pad (M.A.P.), Moisture Alert Pad Pillowcase (M.A.P.P.) and Moisture Alert Pad Vest (M.A.P.V.) will detect any kind moisture or liquid. The pads have technology that will allow the monitor and the person, animal, equipment or object being monitored, to use quicker and multiple wireless options of technological notifications.

(2) Moisture Alert Pad (M.A.P.), Moisture Alert Pad Pillowcase (M.A.P.P.) and Moisture Alert Pad Vest (M.A.P.V.) can be used on any flat surface, mattress, are with an incline, movable surfaces above and under all types of absorbent materials. Bed-written people, animals, etc can alert monitor that they have soiled themselves and it has leaked through their undergarments to M.A.P.

(3) Moisture Alert Pad Pillowcase will detect moisture from the neck and above. The technology will alert the monitor to immediately provide assistance to the person, animal or object being monitored.

(4) All Moisture Alert Pad (M.A.P.), Moisture Alert Pad Pillowcase (M.A.P.P.) and Moisture Alert Pad Vest (M.A.P.V.) are advanced in today's technology to alert the person or object releasing the moisture, along with the monitor that moisture (urine, vomit, water, oil, blood, etc.) was released and detected.

(5) The monitor of the Moisture Alert Pad (M.A.P.), Moisture Alert Pad Pillowcase (M.A.P.P.) and Moisture Alert Pad Vest (M.A.P.V.) can be notified by vibration, light, sound, alarm, alerts, texting, email, wireless tablet, wireless cell phone, instant messaging, phone application, paging options, landline phone, desktop computer, voice notification and other data transmitting and receiving options.

(6) Moisture Alert Pad (M.A.P.), Moisture Alert Pad Pillowcase (M.A.P.P.) and Moisture Alert Pad Vest (M.A.P.V.) can have other shapes and sizes to meet most detection needs. Also moisture detection can be observed on both sides of M.A.P. and M.A.P.P.

(7) Moisture Alert Pad (M.A.P.), Moisture Alert Pad Pillowcase (M.A.P.P.) and Moisture Alert Pad Vest (M.A.P.V.) can detect moisture whether urine, blood, sweat, water, vomit, etc., from a person, equipment, object and/or animal as long as the part of the body or is in direct contact on the pad, pillowcase, and vest.

(8) Moisture Alert Pad (M.A.P.), Moisture Alert Pad Pillowcase (M.A.P.P.) and Moisture Alert Pad Vest (M.A.P.V.) has the capability to store data, print out data, compile data and sent out data per downloadable software and use other technological options. This software is specially designed for M.A.P., M.A.P.P. and M.A.P.V. wireless technology, computerized system, servers and data transmissions.

(9) Most important, being able to be notified from M.A.P., M.A.P.P. and M.A.P.V. can alert the monitor that some type of moisture has been detected and allows them to check to see if leakage of some kind, an uncomfortable state and/or duress situation has occurred. These devices and technology will provide immediate assistance to an infant, child, teen, adult, elderly, equipment, objects and/or animal in need. With the wireless notifications and alert options, can mean the difference between preventing a flood, oil spill and/or the difference in seconds of saving a life where needed.

The invention claimed is:

1. A device for detecting moisture comprising:
a detection layer, a base, a control device, and a cord;
said detection layer comprises a first outer surface and a second outer surface, said first outer surface and said second outer surface having a plurality of sensor divots disposed therein to detect moisture wherein at least a portion of the opposing sides of the outer surfaces are joined together to create a sleeve; and
a plurality of circuits disposed between said first outer surface and said second outer surface and being connected to said sensor divots, said plurality of circuits being insulated; and
a first inner conductive layer and a second inner conductive layer being disposed between the first outer surface and said second outer surface; and
said plurality of circuits being connected to said base, wherein the base is configured to receive a moisture detection signal from said plurality of circuits; and
wherein the cord is attached to the base and connected to the control device;
said control device receiving said moisture detection signal from said base and notifying a user that said moisture has been detected.

2. The device of claim 1 wherein said control device provides a visual, auditory or tactile alert to said user.

3. The device of claim 2 wherein said control device comprises a wireless transmitter.

4. The device of claim 3 wherein said wireless transmitter transmits said alert to a wireless receiving device.

5. The device of claim 4 wherein said wireless receiving device comprises a paging device, a wall monitoring device, a computer, a cell phone or a server.

6. The device of claim 1 wherein said moisture is selected from the group consisting of sweat, blood, urine, saliva, mucus, stomach acid, vomit, oil, and water.

7. The device of claim 1 wherein said device comprises a pillow case covering.

8. The device of claim 1 wherein said control device further comprises a quick response code.

9. The device of claim 1 wherein said first insulating layer and said second insulating layer comprise a nonabsorbent and compressible material.

10. A method for detecting moisture comprising:
providing said device of claim 1; and
detecting moisture when said moisture comes into contact with said device of claim 1; and
alerting a user that said moisture has been detected.

11. The method of claim 10 wherein said alert comprises a visual, auditory or tactile alert.

12. The method of claim 10 wherein said device of claim 1 further comprises a wireless transmitter, said wireless transmitter transmitting said alert to a wireless receiving device.

13. The method of claim 10 wherein said device of claim 1 comprises a bed pillow.

14. The method of claim 10 wherein said device of claim 1 is in contact with a piece of equipment suspected of having a leak.

15. The method of claim 10 wherein said device of claim 1 is in contact with a piece of equipment requiring leakage monitoring.

* * * * *